(12) United States Patent
Amir et al.

(10) Patent No.: US 9,134,277 B2
(45) Date of Patent: Sep. 15, 2015

(54) APPARATUS AND METHOD FOR REAL TIME MONITORING OF TUBE SYSTEMS

(75) Inventors: Noam Amir, Ness-Ziona (IL); Tal Pechter, Ramat-Hasharon (IL)

(73) Assignee: ACOUSTICEYE LTD, Tel Aviv (IL)

( * ) Notice: Subject to any disclaimer, the term of this patent is extended or adjusted under 35 U.S.C. 154(b) by 514 days.

(21) Appl. No.: 13/510,095

(22) PCT Filed: Nov. 17, 2010

(86) PCT No.: PCT/IL2010/000959
§ 371 (c)(1),
(2), (4) Date: May 16, 2012

(87) PCT Pub. No.: WO2011/061739
PCT Pub. Date: May 26, 2011

(65) Prior Publication Data
US 2012/0227499 A1    Sep. 13, 2012

Related U.S. Application Data

(60) Provisional application No. 61/263,377, filed on Nov. 22, 2009.

(51) Int. Cl.
*G01N 29/07*     (2006.01)
*G01N 29/04*     (2006.01)
*G01M 3/24*      (2006.01)
*G01M 5/00*      (2006.01)

(52) U.S. Cl.
CPC ............... *G01N 29/043* (2013.01); *G01M 3/24* (2013.01); *G01M 3/243* (2013.01); *G01M 5/0025* (2013.01); *G01M 5/0033* (2013.01); *G01M 5/0066* (2013.01); *G01N 2291/044* (2013.01); *G01N 2291/2634* (2013.01)

(58) Field of Classification Search
CPC .......... G01N 29/043; G01N 2291/044; G01N 2291/2634; G01N 2291/2636; G01M 3/24; G01M 3/243; G01M 5/0025; G01M 5/0033
USPC ................................. 73/592, 597, 598, 40.5 A
See application file for complete search history.

(56) References Cited

U.S. PATENT DOCUMENTS

| 2,568,926 A | 9/1951 | Moran |
| 5,883,815 A | 3/1999 | Drakulich et al. |
| 6,453,247 B1 * | 9/2002 | Hunaidi .................. 702/51 |

(Continued)

OTHER PUBLICATIONS

International Search Report for PCT/IL2010/000959 dated Mar. 15, 2011.

*Primary Examiner* — Laura Martin
*Assistant Examiner* — Rose M Miller
(74) *Attorney, Agent, or Firm* — Smith Risley Tempel Santos LLP; Gregory Scott Smith

(57) ABSTRACT

The internal state of a tube system is detected and monitored by coupling multiple inspection modules to the tube system. Each inspection module injects a signal into the tube system and detects reflections of the signals. The distance between the module and the fault causing a reflection is determined by analyzing the timing between the transmitted signal and detected reflection, along with a known propagation speed of the signals. The location of faults is determined by comparing the distance calculations from two or more inspection modules. Monitoring can be performed over time to identify the development or changes of faults. Monitoring can be done while tube system is active without disrupting the flow of material through the active tube system.

18 Claims, 7 Drawing Sheets

(56) References Cited

U.S. PATENT DOCUMENTS

| | | | |
|---|---|---|---|
| 6,705,319 B1 * | 3/2004 | Wodicka et al. | 128/207.14 |
| 7,475,596 B2 * | 1/2009 | Hunaidi et al. | 73/592 |
| 2002/0167414 A1 | 11/2002 | Kelly | |
| 2003/0033879 A1 * | 2/2003 | Adewumi et al. | 73/627 |
| 2007/0034012 A1 | 2/2007 | Amir et al. | |
| 2007/0286024 A1 | 12/2007 | Raphael | |
| 2008/0208505 A1 | 8/2008 | Amir et al. | |
| 2009/0196122 A1 | 8/2009 | Crowell | |
| 2009/0250125 A1 * | 10/2009 | Howitt | 137/551 |
| 2011/0112776 A1 * | 5/2011 | Amir et al. | 702/56 |
| 2013/0332091 A1 * | 12/2013 | Amir et al. | 702/56 |

* cited by examiner

APPARATUS AND METHOD FOR REAL TIME MONITORING OF TUBE SYSTEMS

CROSS-REFERENCE TO RELATED APPLICATIONS

This is a non-provisional utility application being filed with the United States Patent Office under 35 USC 371 and is based on the Patent Cooperation Treaty application that was filed under Article 3 of the Patent Cooperation Treaty on Nov. 17, 2010, assigned International Serial Number PCT/IL2010/000959 and which claims priority under Article 8 of the Patent Cooperation Treaty and Article 4 of the Paris Convention of the prior filing date of the United States Provisional Application for patent that was filed in the United States Patent Office on Nov. 22, 2009 and assigned Ser. No. 61/263,377, each of these applications are incorporated herein by.

BACKGROUND

Tube systems have been employed or unitized in a wide variety of different applications. A few non-limiting examples of such applications include chemical industries/plants, power stations, semiconductor fabrication industries, food and beverage industries, and many more. In most of these applications, the tubes are susceptible to developing a variety of faults, depending on their operating conditions. Some of the common faults may include leaking connectors, stuck valves, accumulation of deposits, bulges, corrosion etc. Many techniques have been developed in an effort to monitor or inspect the current conditions of such tube systems. Some of these inspection techniques must be performed in an "off-line" setting. Thus, to perform the inspection, the application employing the tube system is required to be shutdown or stopping the processes taking place in these tube systems. Employing such techniques can be quite costly and disruptive. Other inspection techniques can be performed in an on-line or operational system without interrupting the processes in the tube systems. Examples of such on-line techniques can include "sniffers" that operate to detect leaking substances, or acoustic emission techniques which examine the noise emitted by the tube systems. Such currently available on-line techniques are deficient in that they provide limited accuracy.

Thus, there is a need in the art for a solution for inspecting tube systems that can continuously monitor the tube systems while in operation (on-line), at any time, and that provide a high degree of accuracy with regards to identifying faults, determining the location of such faults and identifying the type of fault.

BRIEF SUMMARY

In addressing the above-described needs in the art, as well as other needs and/or short-comings in current technology, the present disclosure presents an inspection solution that operates to monitor a tube system in real-time and during on-line operation. Throughout this description, the term real-time refers to monitoring and/or inspecting the tube system while the tube system is on-line or operating in a normal fashion without impeding or affecting its operation. Advantageously, the operation of the tube system is not disturbed and indications of faults can be detected and received close to the time that they occur.

Exemplary embodiments of the inspection system, which refers to both a system and a method of performing the described inspection techniques, can include inserting monitoring components directly into the tube system itself or coupling monitoring components to the tube system. Such components, which are referred to as the "active components", may operate to monitor the elements of the tube system in their vicinity and generate data regarding the tube system status and deliver the data and/or generate reports based on the data. The resultant information can be transmitted to a central station that can operate to compile, analyze and assimilate the information from all the active components in the system. The information may be delivered in a variety of manners including all variants of wired or wireless connections, as well as transportation via storage mediums or shared databases. The monitoring that can be performed by a single such active component is based on Acoustic Pulse Reflectometry (APR) which has been described in a patent application filed in United States and assigned Ser. No. 11/996,503. The afore-mentioned patent application is included herein by reference.

DETAILED DESCRIPTION OF EMBODIMENTS OF THE INVENTION

Several exemplary embodiments of a real time innocuous inspection system based on the use of Acoustic Pulse Reflectometry (APR) technology are presented. An exemplary APR based inspection system for Non-Destructive Testing (NDT) of tubular systems has been described in detail in a patent application filed in the United States and assigned Ser. No. 11/996,503 the content of which incorporated herein by reference.

Figure 1:
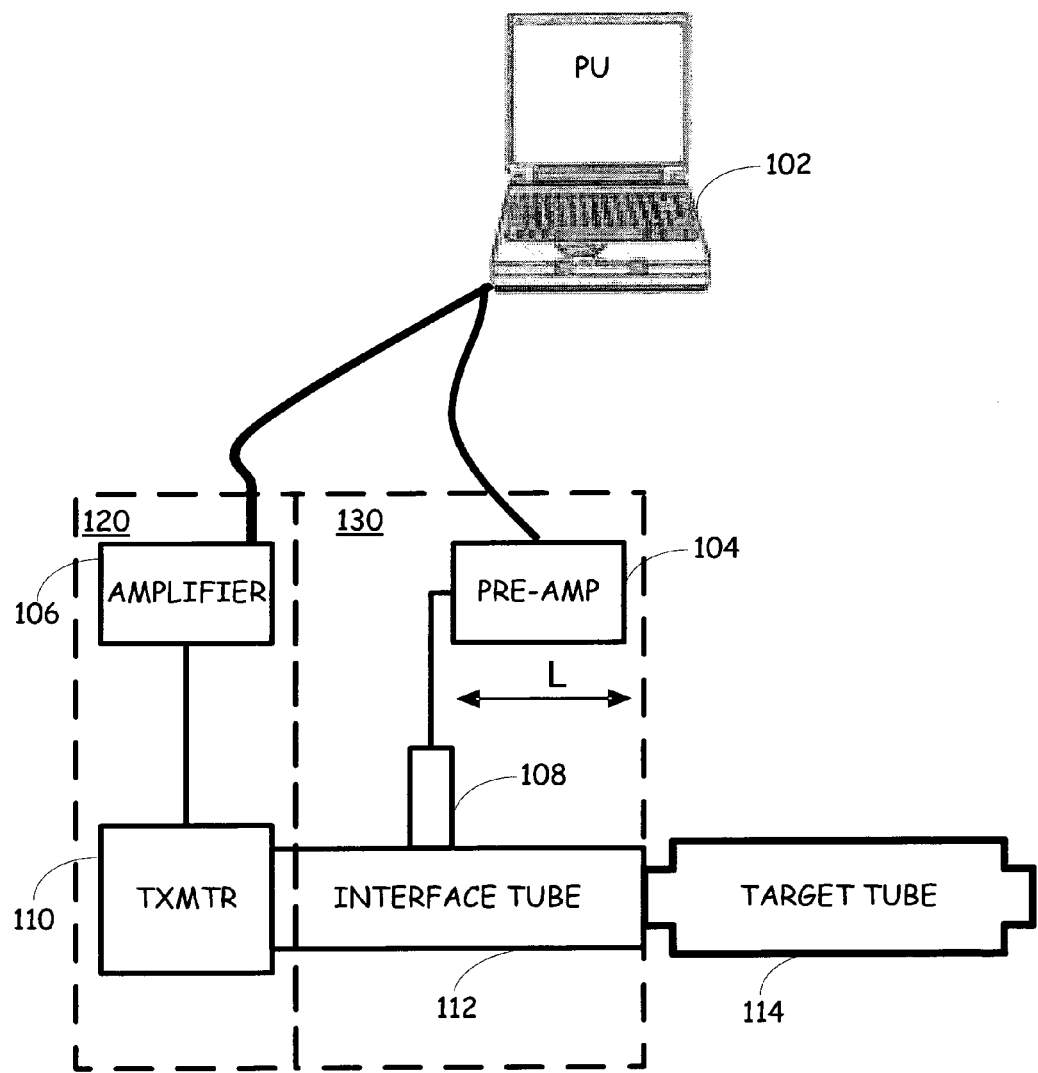
FIG. 1 shows a block diagram with relevant elements of an exemplary inspection system employing APR technology for the provision of innocuously-testing or inspection of tubes.

FIG. 1 shows a block diagram with relevant elements of an exemplary inspection system employing APR technology for the provision of innocuously-testing or inspection of tubes. The illustrated embodiment includes a signal injector 120 and a signal detector 130. The signal injector 120 is configured to inject a signal into a medium, or interface tube 112, which acts as an interface to the target tubes being tested 114. The signal can be an acoustic wave for example. In other embodiment the signal can be electro-magnetic wave. The wave then propagates into the target tubes. The signal detector 130 includes a sensor 108 that detects signals reflected back from the target tubes 114 into the interface tube 112. The signal injector 120 and signal detector 130 may operate as a stand-alone unit, a stand-alone unit that interfaces and/or reports information to other system, by an external processing unit 102 such as a personal computer, as well as other structures and/or configurations. For instance, in the stand-alone configuration, a processing unit may be incorporated into the signal injector 120 and/or the signal detector 130. In such embodiments, the processing unit may be as simple as a microcontroller, an ASIC or even simply analog and/or digital control circuitry. The stand-alone unit may include a user interface for initiating a test sequence or, it may simply be activated by coupling the interface tube 112 to a tube under test 114. The recorded signal may be stored in internal memory and/or information regarding the detection may be displayed to a user in a variety of manners including the use of an LCD or even simple codes displayed using lights or numbers, or audible sounds such as error codes or certain tones or buzzers may also be used.

The exemplary inspection system that is shown in FIG. 1 can comprise the processing unit 102 that synthesizes an acoustic signal which is transmitted through a transmitter 110 via an amplifier 106. The acoustic signals converted into an acoustic wave by the transmitter 110. The acoustic wave first propagates down an interface tube 112, where it is recorded by an exemplary pressure sensor 108. The acoustic wave then travels down a target tube 114, or a tube that is being subject to inspection, monitoring or examination. Any change in the cross-section of the interior of the tube will result in causing a reflection that will propagate back up target tube 114 and interface tube 112, to be recorded by pressure sensor 108. The recoded signal can be amplified by a pre-amp 104, be converted into digital data and then stored, or information about such reflection being stored, by processing 102. The recorded reflections are analyzed by software applications being executed by processing 102 or another computing system, in order to identify the faults that created them, such as blockages (full or partial), pitting, general wall loss, bulges and holes.

Figure 2:
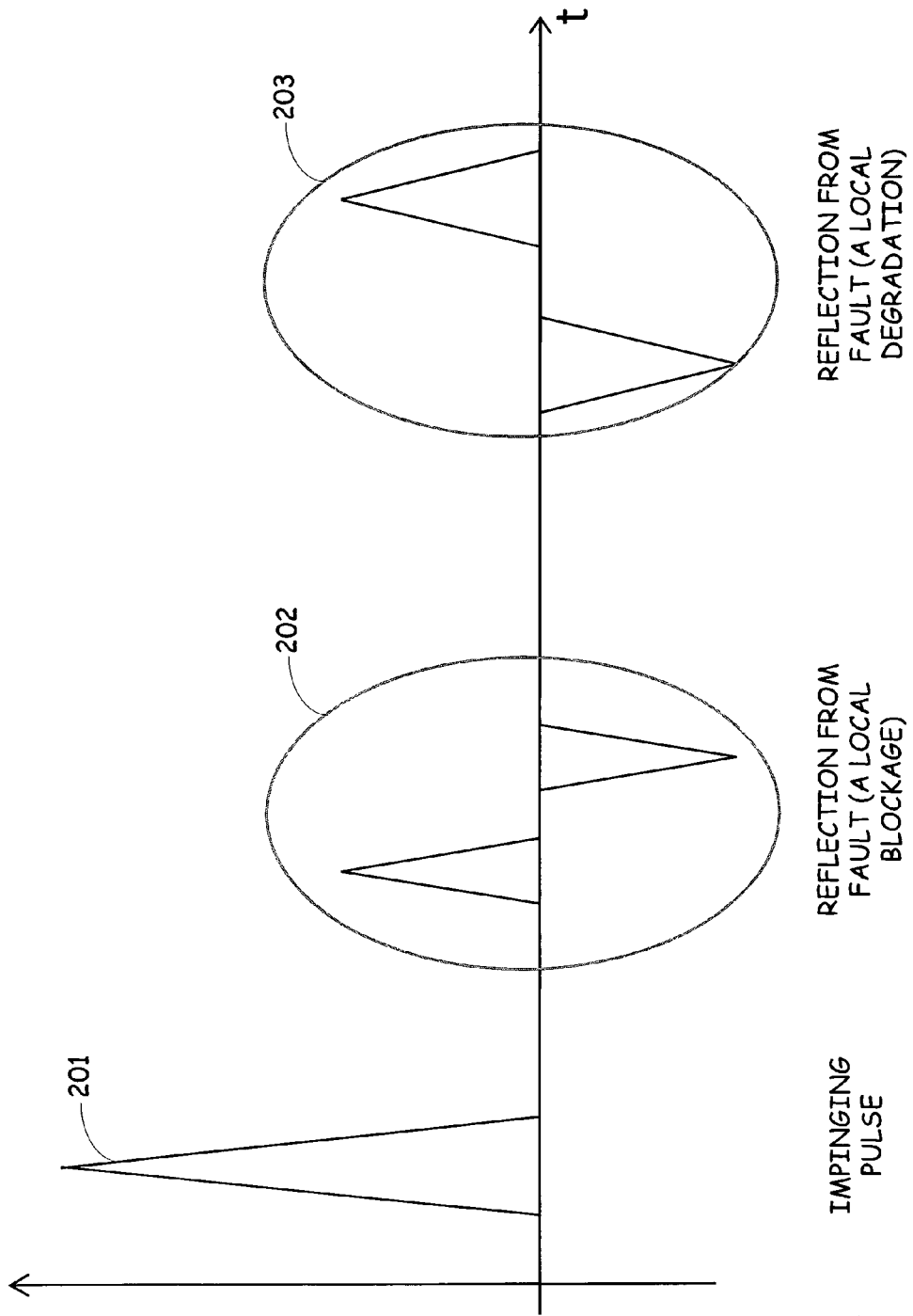
FIG. 2 illustrates typical reflections from a local blockage and a local degradation obtained by an exemplary APR based inspection system.

FIG. 2 illustrates typical reflections from a local blockage and a local degradation obtained by an exemplary APR based inspection system. FIG. 2 gives schematic examples of the reflections from different faults. For an impinging pulse 201 such as a sharp positive pulse as depicted in FIG. 2, the reflection from a local blockage will appear as a positive pulse (reflected from the leading edge of the blockage) followed by a negative pulse (reflected from the terminating edge of the blockage) as shown in reflection 202 from a local blockage. A reflection from pitting or erosion or a bulge will include a negative pulse (reflected from the leading edge of the wall loss) followed by a positive pulse (reflected from the terminating edge of the wall loss) as shown in reflection 203 from a local degradation. Processing the results in the exemplary APR system can comprise searching for isolated incidences of such reflections, quantifying them and reporting them.

Figure 3:
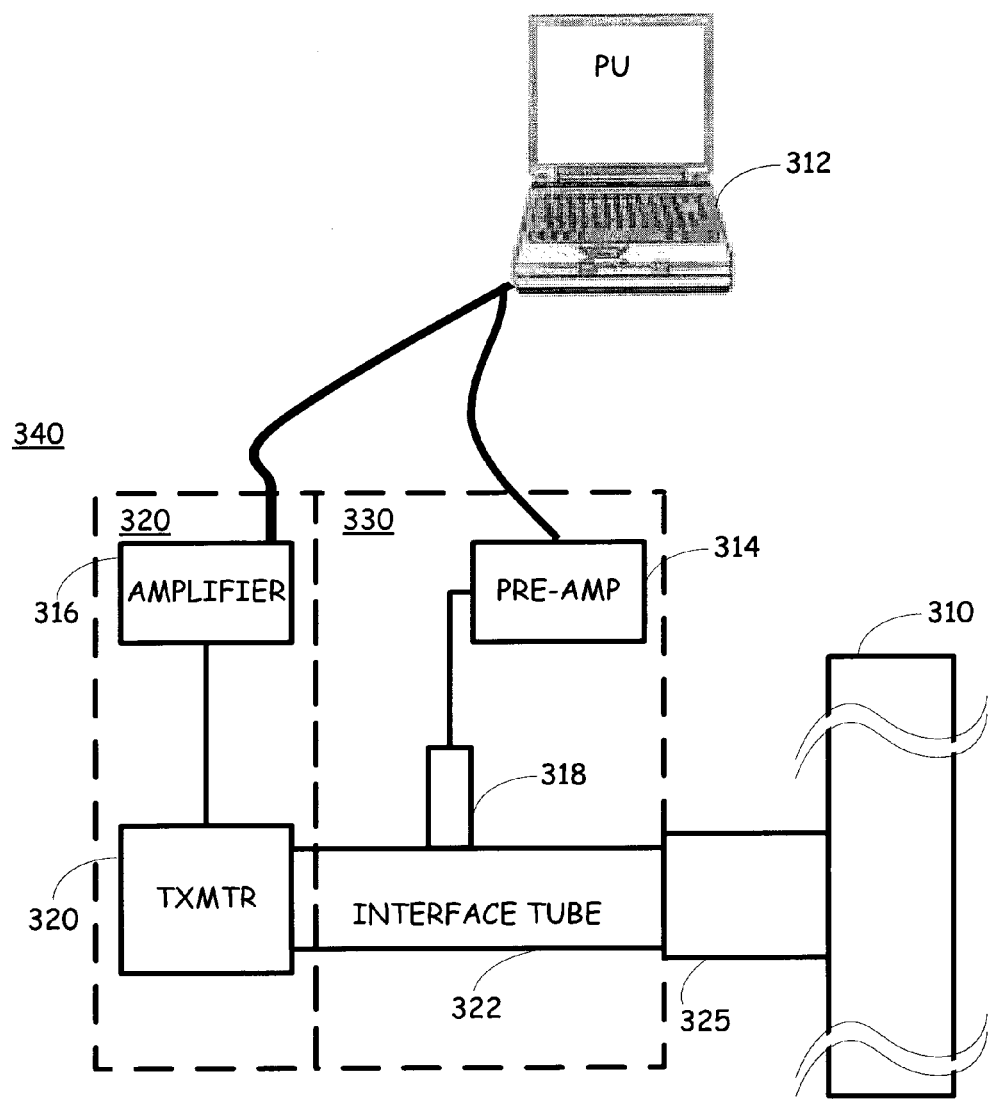
FIG. 3 shows a block diagram with relevant elements of an exemplary APR based inspection system providing real-time monitoring of a tube system.

FIG. 3 shows a block diagram with relevant elements of an exemplary APR based inspection system providing real-time inspection and/or monitoring of a tube system. The illustrated embodiment includes an inspection module 340 that includes a signal injector 320 and a signal detector 330. The signal injector 320 is configured to inject acoustic wave, for example, into a medium, or interface tube 322, which, along with a connector 325, acts as an interface to the target tube system 310 that is being monitored. The inspection module is coupled to the tube system in a non-disruptive or innocuous fashion such that the flow of liquid or gas through the tube system is not disrupted or is minimally and/or negligibly impacted. Thus, in one embodiment, a coupler 325 is connected to the tube system through a hole or portal in one of the tubes of the tube system 310. In some embodiments, the coupler 325 may include a tapping mechanism that can be attached to a tube of the tube system and pierce into the tube system 310. In other embodiments, a T-coupler (see element 404 of FIG. 4 described below) can be installed in-line with one of the tubes of the tube system 310.

The signal detector 330 may include a sensor 318 that detects signals reflected back from the target tubes 310 into the interface tube 322 through the coupling mechanism 325. The signal injector 320 and signal detector 330 may operate as a stand-alone unit, a stand-alone unit that interfaces and/or reports information to another system, in other embodiments an external processing unit can be used for controlling the signal injector 320 and signal detector 330, as well as other structures and/or configurations. For instance, in the stand-alone configuration, a processing unit may be incorporated into the signal injector 320 and/or the signal detector 330. In such embodiments, not showing in the drawings, the processing unit may be as simple as a microcontroller, an ASIC or even simply analog and/or digital control circuitry. The stand-alone unit may include a user interface for initiating a test sequence or, it may simply be activated by coupling the interface tube 322 to a tube system under test 310. Measured information may be stored in internal memory and/or information regarding the detection may be displayed to a user in a variety of manners including the use of an LCD or even simple codes displayed using lights or numbers, or audible sounds such as error codes or certain tones or buzzers may also be used. In the embodiment illustrated in FIG. 3, the real-time inspection and/or monitoring NDT system, monitors the status of a tube system 310. The illustrated NDT system can comprise a processing unit 312, a preamplifier 314, an amplifier 316, a pressure sensor 318, a transmitter 320, and an interface tube 322. The tube system 310 illustrated represents only a segment of a much larger system that may contain various connected tubes of various lengths. In order to be connected in real-time to the tube system 310, an exemplary NDT system can be connected through a branched connector 325 as shown in FIG. 3. In this manner the tube system 310 can maintain normal flow of whatever gas or fluid is necessary while still allowing access to the transmitter 320 and pressure sensor 318. In the exemplary real-time NDT system, the acoustic wave created by transmitter 320, upon reaching tube system 310 will split and propagate in opposite directions (up and down or left and right) in the diagram. Reflections of the signal that occur in the tube system 310 will arrive back at pressure sensor 318, via the branched connector 325, from both branches of the tube system 310. For instance, a reflected signal will propagate through the tube system 310 and then split and entering into the interface tube 322 and the rest of the reflective wave can further propagate through the tube system 310.

Distance measurements can be obtained by an exemplary NDT system, in which a single APR module 340 is used, by determining the physical distance of a fault from the sensor 318. The calculation can be done by measuring the duration of time (the time of flight) between transmitting the signal (transmitted at time t1) and the time (detected at time t2) of receiving a reflection from the fault. The timing information, along with known or calculable propagation speeds of the transmitted signals enable the system to determine the distance between the APR module 340 and a fault that is causing the reflection.

Figure 4:
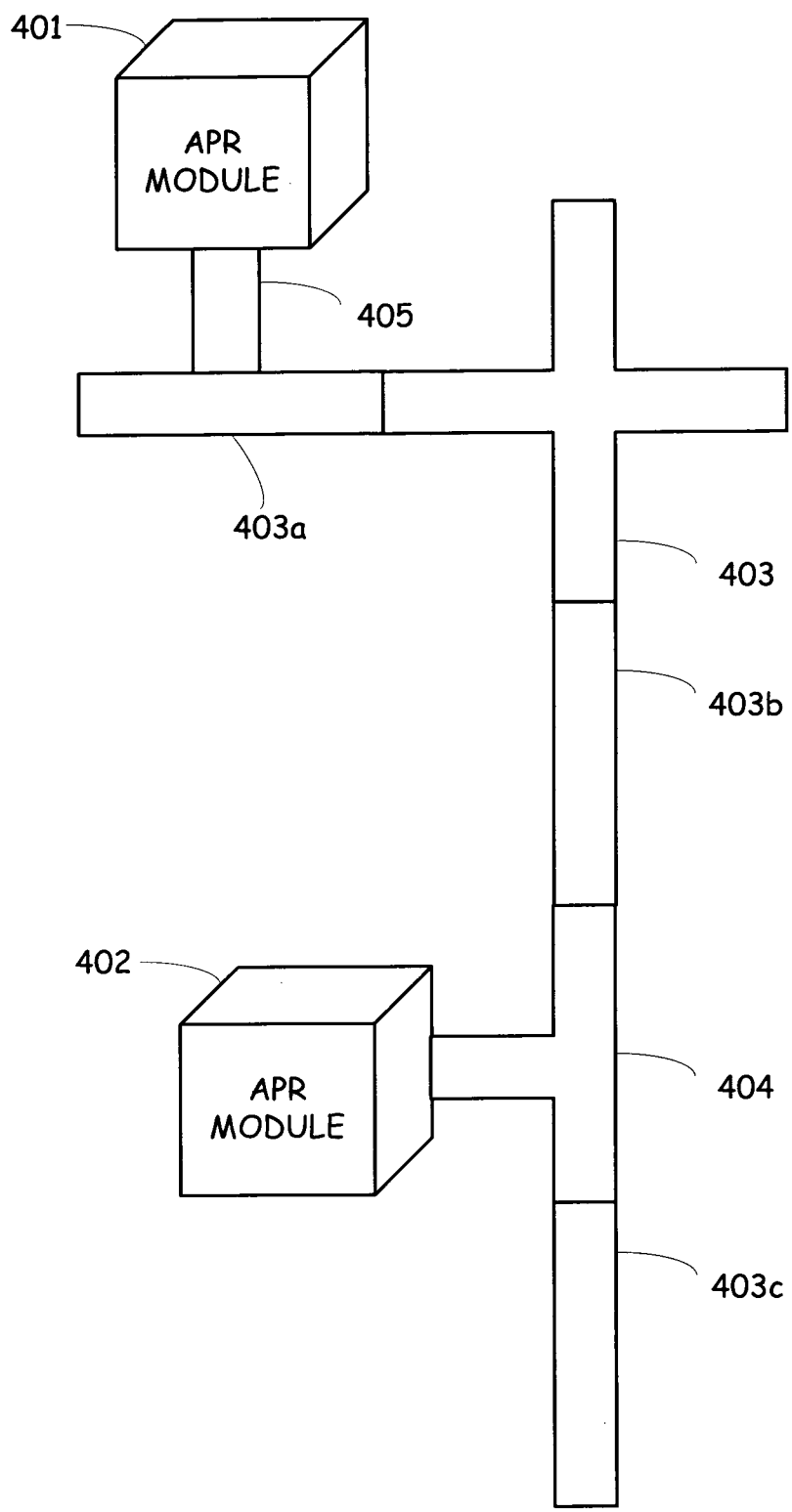
FIG. 4 shows another exemplary embodiment of the inspection system in which two APR components in a segment of the tube system are illustrated.

FIG. 4 shows another exemplary embodiment of the inspection system in which two APR modules in a segment of the tube system are illustrated. More specifically, FIG. 4 illustrates another exemplary embodiment of a real-time NDT system that can give an indication from which branch the reflection was received from a tubular system 403 (where various segments of the tube system are identified by the common identifier 403). The exemplary system can comprise a plurality of APR modules 401, 402 installed in or coupled to the tubular system at various locations. APR module 401 is shown as being coupled to the tube system 403 through a coupler 405 that is coupled through a hole, portal or tap into the side of tube segment 403a. APR system 402 is shown as being coupled to the tube system 403 by a T-connector 404 that is inserted in-line between tube segments 403b and 403c. Each one of the APR modules can be connected to a central computer or processing unit (not shown in the drawing). Each APR module 401, 402 can comprise the components as illustrated in FIG. 3, including the preamplifier 314, amplifier 316, pressure sensor 318, transmitter 320, and interface tube 322 (FIG. 3). The information from the plurality of the APR modules can be analyzed in combination with each other to determine the true source of reflections indicating faults. It should be noted that in FIG. 4, two APR modules (401, 402) are shown only by way of example. It will be appreciated by a person of ordinary skill in the art that a number of APR modules other than two can be used in accordance with various embodiments of the NDT system. It will also be appreciated that in some embodiments, the sensor 318 can be used to both detect signals in the system as well as inject signals into the system. For instance, a transducer that generates acoustic waves from electric signals and generates electric signals from acoustic waves may be used as a single device. Furthermore, it should be appreciated that the sensor 318 can be coupled directly to the tubing system 310 or a segment of the tubing system 310. It should also be appreciated that in some embodiments, multiple sensors 318 may be used and positioned at selected locations throughout the tubing system to detect signals and reflected signals. In yet another embodiment employing the use of a bi-direction transducer as described above, the interface tube 322 and coupling tube 325 can be eliminated with the transducer or sensor being mounted direction to the tubing system 310 for injecting a signal and detecting reflected signals.

Figure 5:
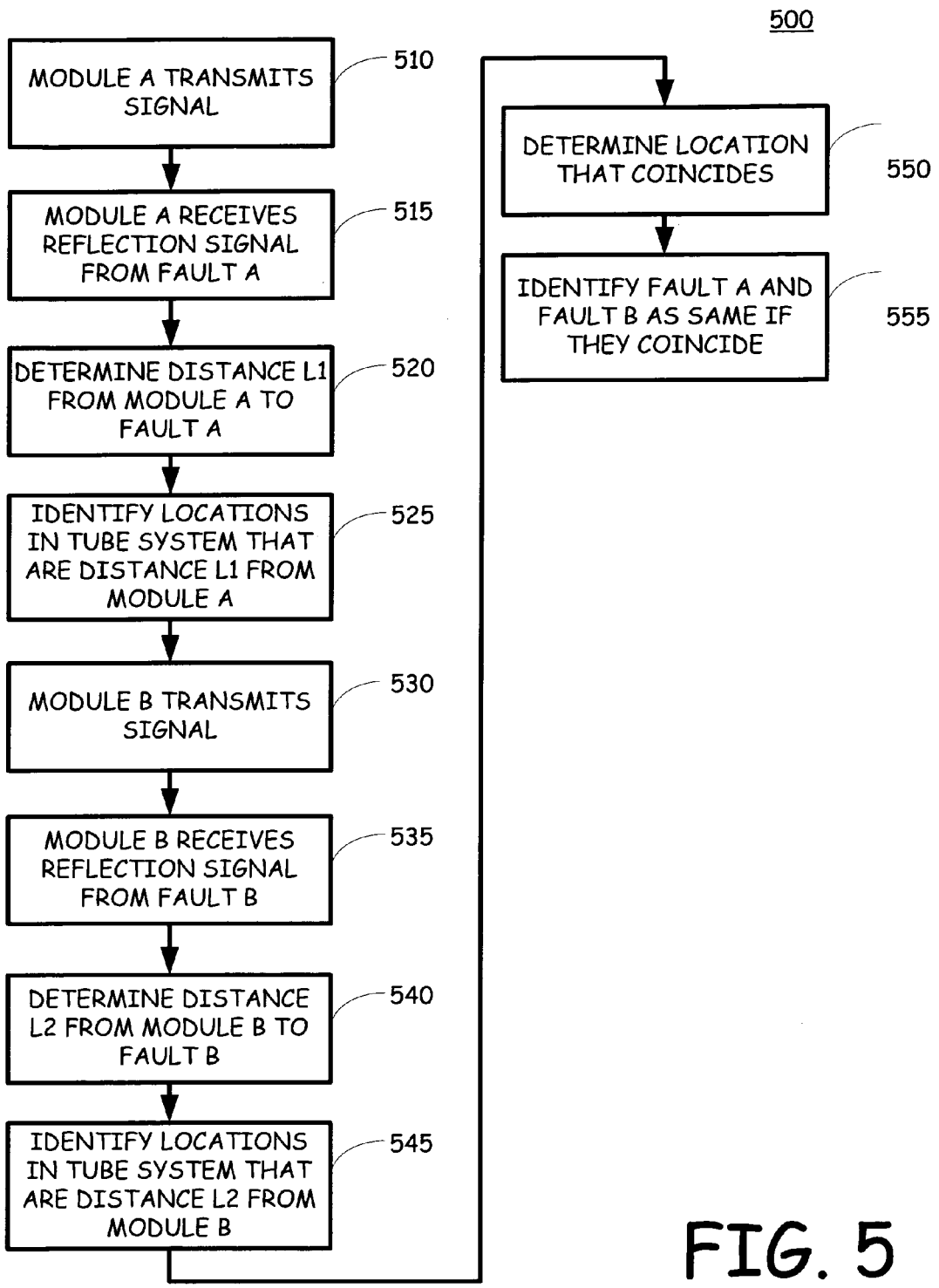
FIG. 5 is a flow diagram illustrating actions that can be performed using multiple APR modules to identify the location of faults within a tube system.

FIG. 5 is a flow diagram illustrating actions that can be performed using multiple APR modules to identify the location of faults within a tube system. When measurements are obtained by exemplary NDT systems in which several different APR modules are used, cross-comparison between results can be used to determine where the physical fault is actually located. For the example of FIG. 4, when multiple modules are installed, an exemplary location identification process could operate by performing the following actions:

(1) Module A transmits 510 an acoustic wave at time t1 into the tube system.

(2) Module A, receives 515a reflection signal from a fault (fault A).

(3) Determine 520 the distance L1 between the module A and the fault A using time of flight of the signal.

(4) In response to the information obtained by module A, each of the points that are the distance L1 from this module A are identified 525.

(5) Module B transmits 530a signal at time t2 into the tube system.

(6) Module B, receives 535a reflection signal from a fault (fault B).

(7) Determine 540 the distance L2 between the module B and the fault B, using time of flight of the signal.

(8) In response to the information obtained by module B, each of the points that are the distance L2 from this module B are identified 545.

(9) The identified points that are a distance L1 from module A and L2 from module B can be compared 550 to find common locations in the tube system, or a point that coincides.

(10) When a point located a distance L1 from module A coincides with a point located distance L2 from module B, and both signals indicate that they are reflected from a similar type of fault, it can be deduce 550 that this point is the location of the fault and that fault A and fault B are the same fault.

In some embodiments the APR modules (401, 402 . . . ) can be installed at intervals along the tube system. In other embodiments the APR modules (401, 402 . . . ) can be installed near locations deemed to be more prone to faults. The APR components do not affect, or have insignificant affects on the normal flow of fluids or gasses in the tube system.

It should be noted that although the actions described in FIG. 5 are shown as being sequential, they are not specifically required to be performed in the illustrated ordering.

In various embodiments employing multiple APR modules to inspect or monitor a tube system, techniques can be employed to prevent false signal detections. For instance, in one embodiment, the various modules may transmit their signals in a time-division fashion. Thus, each module may transmit its signal and receive reflections while the other modules remain idle or inactive. In such embodiments, each module may have a given time-slot in which to transmit its signal and receive reflections. In other embodiments, modules that are located at minimal distances from each other may share a time-slot. In yet other embodiments, the modules may transmit at the same time but use various signal types, frequencies or shapes of signals so that signal transmissions from module X and reflections of that signal will not be received and mistakenly identified by module Y as a reflection of a single transmitted by module Y. In other embodiments, multiple modules may be positioned at strategic positions along the tubing system 310 such that signals from one module would not interfere with the detection of signals by another module. For instance, the distance between the inspection modules may be such that signals from one module are not detected by another module and incorrectly confused with a reflection (false detection). It should also be appreciated that signal processing can be performed to differentiate reflected signals from transmitted signals. Various embodiments may also include combinations of any of these techniques as well as other techniques.

In various embodiments of the NDT system, the APR components can be periodically activated and their measurements can be transmitted or provided to a central processor. At the central processor, the measurements from the different components can be combined and analyzed. Regular activation and archiving of the results advantageously enables the NDT system to compare the changes encountered over time, and thus, the NDT can detect and assess whether fault mechanisms are developing in the tube system. The ability to see faults development as a process rather than obtaining an occasional snapshot when using other testing methods contributes in discovering and understanding fault mechanisms and avoiding catastrophic failures.

In some exemplary embodiments each APR module 401 can include its own dedicated computer or processing unit, such as processing unit 312 in FIG. 3. In such embodiments the results of each APR module can be analyzed locally in its local computer and the results can be transmitted to a central processor where the measurements from the different components are combined and analyzed.

It should be appreciated that various embodiments of the NDT system can be implemented for tubular systems filled with gas or liquid, as well as tube systems that are pressurized or non-pressurized. In addition, the various embodiments of the NDT system can be employed in tube systems containing gas or liquid at any temperature so long as the temperature does not threaten the integrity of the components. In some embodiments of the NDT system, the APR modules might have continuous access or fluidity with the tube system but, in other embodiments, the APR modules may be selectively blocked off from the operative part of the tubing system using valves or similar mechanisms that can be opened at the time of inspection and then shut again. These valves can be operated either manually, mechanically or electronically, either locally or remotely, and may be controlled manually or by a processing unit.

Figure 6:
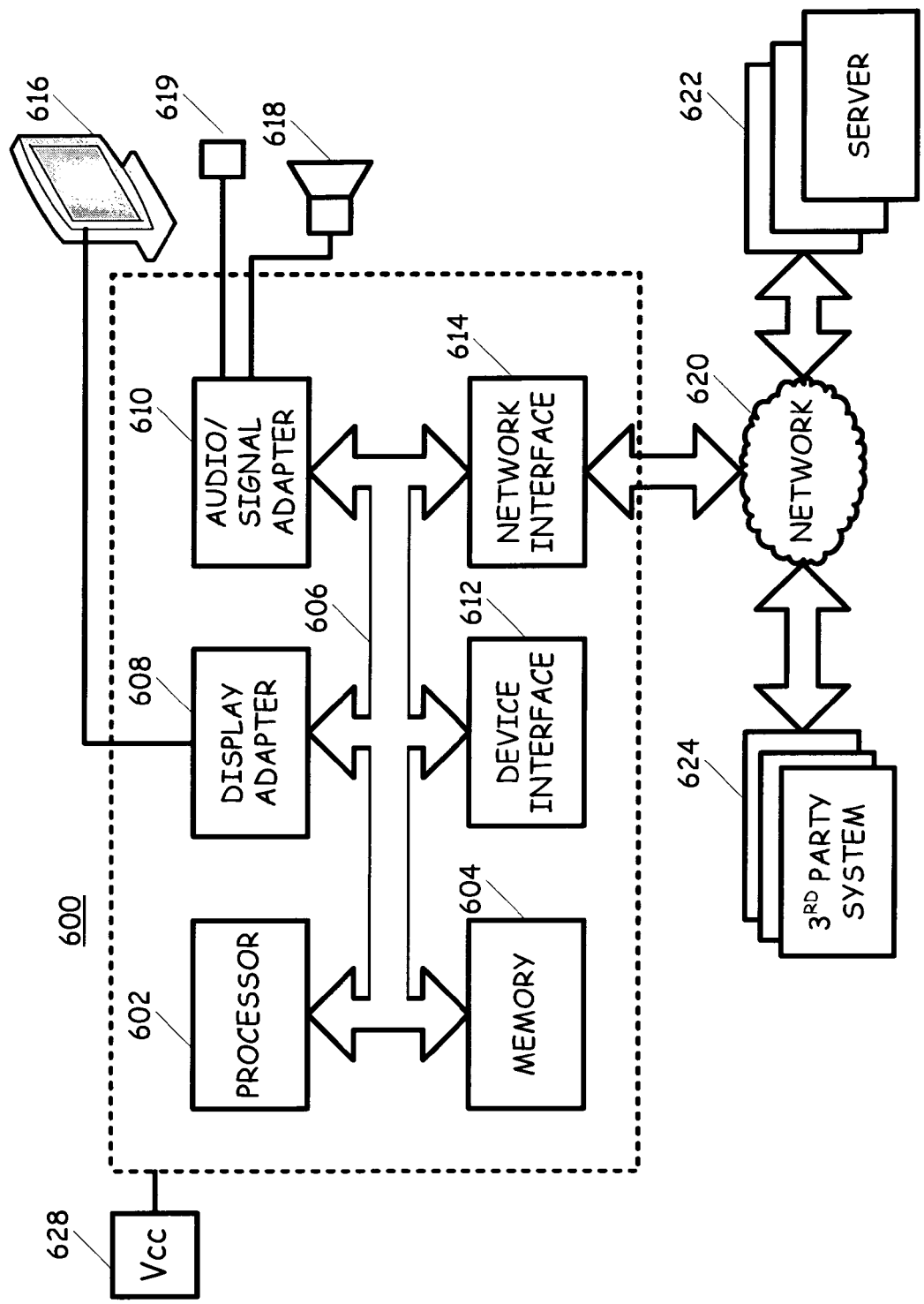
FIG. 6 is a functional block diagram of the components of an exemplary embodiment of the measuring system, as well as other embodiments thereof.

FIG. 6 is a functional block diagram of the components of an exemplary embodiment of the measuring system, as well as other embodiments thereof. It will be appreciated that not all of the components illustrated in FIG. 6 are required in all embodiments of the measuring device but, each of the components are presented and described in conjunction with FIG. 6 to provide a complete and overall understanding of the components. Further, many specific elements are not presented in FIG. 6 but rather functions and/or functional interfaces are used in a generic fashion to indicate that various embodiments may use a variety of specific components or elements. The measuring system can include a general computing platform 600 illustrated as including a processor 602 and a memory device 604 that may be integrated with each other (such as a microcontroller) or, communicatively connected over a bus or similar interface 606. The processor 602 can be a variety of processor types including microprocessors, micro-controllers, programmable arrays, custom IC's etc. and may also include single or multiple processors with or without accelerators or the like. The memory element of 604 may include a variety of structures, including but not limited to RAM, ROM, magnetic media, optical media, bubble memory, FLASH memory, EPROM, EEPROM, etc. The processor 604, or other components may also provide components such as a real-time clock, analog to digital converters, digital to analog converters, etc. The processor 602 also interfaces to a variety of elements including a control or device interface 612, a display adapter 608, audio/signal adapter 610 and network/device interface 614. The control or device interface 612 provides an interface to external controls or devices, such as sensor, actuators, transducers or the like. The device interface 612 may also interface to a variety of devices (not shown) such as a keyboard, a mouse, a pin pad, and audio activate device, a PS3 or other game controller, as well as a variety of the many other available input and output devices or, another computer or processing device. The device interface may also include or incorporate devices such as sensors, controllers, converters, etc. For instance, the amplifier 106, and the preamp 104 illustrated in FIG. 1 could all be included in the device interface 612 either as internal or integrated components or, the device interface 612 may interface to the devices as external components. Alternatively the processing unit 102 illustrated in FIG. 1 could interface to the measuring elements as a stand-alone third party system through control lines, a wired network or a wireless network. The display adapter 608 can be used to drive a variety of alert elements and/or display devices, such as display devices including an LED display, LCD display, one or more LEDs or other display devices 616. The audio/signal adapter 610 interfaces to and drives another alert element 618, such as a speaker or speaker system, buzzer, bell, etc. In the various embodiments of the measuring device, the audio/signal adapter could be used to generate the acoustic signal from speaker element 618 and detect the received signals at microphone 619. The amplifiers, digital-to-analog and analog-to-digital converters may be included in the processor 602, the audio/signal adapter 610 or other components within the computing platform 600 or external there to. The network/device interface 614 can also be used to interface the computing platform 600 to other devices through a network 620. The network may be a local network, a wide area network, wireless network, a global network such as the Internet, or any of a variety of other configurations including hybrids, etc. The network/device interface 614 may be a wired interface or a wireless interface. The computing platform 600 is shown as interfacing to a server 622 and a third party system 624 through the network 620. A battery or power source 628 provides power for the computing platform 140.

Figure 7:
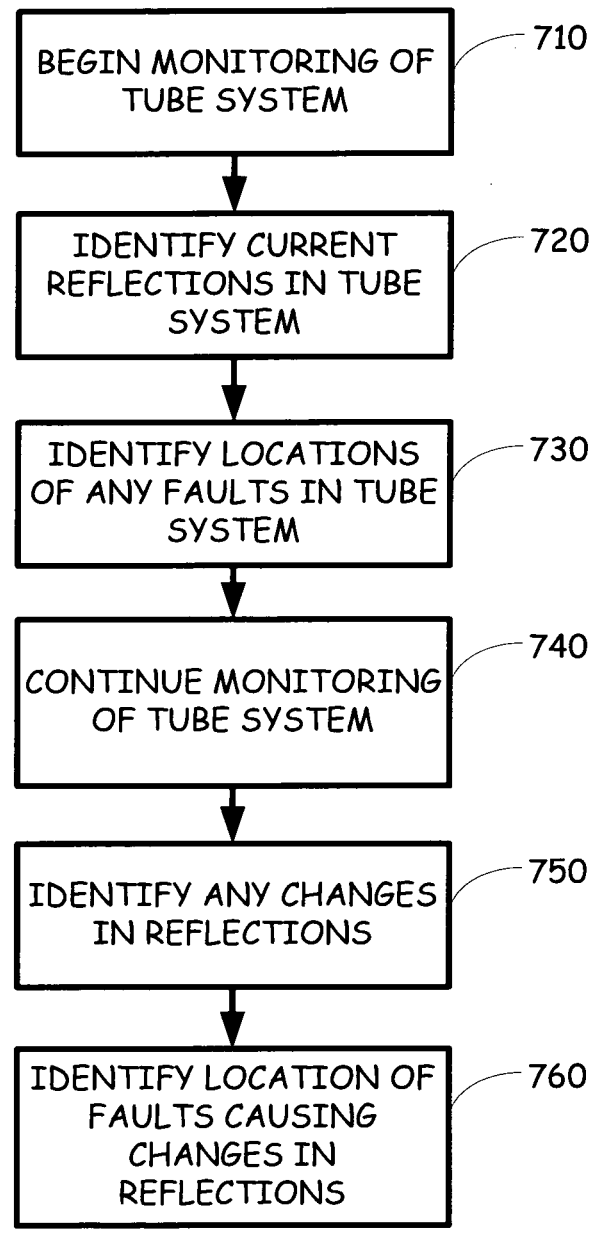
FIG. 7 is a flow diagram illustrating the operation of an exemplary Non-Destructive Testing (NDT) system for monitoring the development and/or changes in faults of a tube system.

FIG. 7 is a flow diagram illustrating the operation of an exemplary NDT system for monitoring the development and/or changes in faults of a tube system. Initially an inspection process is conducted by monitoring the tube system for a period of time 710. The initial monitoring session identifies the current state of the tube system by identifying all elements creating reflection (changes in diameter, fittings, junctions, etc), if any, that exist in the tube system by receiving reflections 720, analyzing the reflections and identifying the location of such elements 730. Once the current state of the tube system is determined, the NDT system continues to monitor the tube system 740. For instance, the inspection modules may be configured to transmit multiple signals over a duration of time, either periodically or not periodically. The NDT system identifies any changes that may be detected in the reflections within the tube system 750 by detecting changes in the characteristics of the reflected signals, detecting new reflected signals or changes in amplitude of pre-existing reflections or detecting the absence of expected reflected signals. For instance, if a change in cross section becomes more pronounced, the intensity of the reflections may be increased. In such an instance, this may be an indication that the deposits are growing or wall loss is occurring). If a reflection becomes less pronounced, this may be an indication that a wall loss has occurred or even wall segments have broken free of the inner surface of the tube system 310 and as such, may need to be filtered out of the tube system 310 to prevent damage or further clogging. Further, if new faults are developed, additional reflections may be detected. The reflection information is analyzed, similar to the process illustrated in FIG. 5, to identify the location of the faults causing the changes in the reflections 760.

It should be appreciated that during the process of identifying the location of a fault, information can be stored to associate particular reflections with particular faults. For instance, if a fault F1 is detected by analyzing the reflection R1 of inspection module A and reflection R2 of inspection module B. Subsequently, in further monitoring of the system, only a single module, such as module A or module B can be used to detect changes in the fault F1. Thus, if module A transmits a signal and detects that the reflection R1 (for which the system may have stored information such as timing of the reflection, amplitude of the reflection, shape of the reflection, type of fault, etc.) has changed, based solely on this information, the system can conclude that the characteristics of the fault have changed.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

In this application the words "unit" and "module" are used interchangeably. Anything designated as a unit or module may be a stand-alone unit or a specialized module. A unit or a module may be modular or have modular aspects allowing it to be easily removed and replaced with another similar unit or module. Each unit or module may be any one of, or any combination of, software, hardware, and/or firmware.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A system that inspects the condition of a tube system for faults, wherein the inspection is performed in real-time on an active tube system without disrupting the flow of material through the active tube system, the system comprising:
    a plurality of inspection modules with each inspection module being coupled to a tube system that is to be inspected;
    one or more processing units communicatively coupled to the plurality of inspection modules;
    each inspection module being configured to inject a signal into the tube system, detect reflections of the signal caused by one or more faults in the tube system and provide information pertaining to the reflected signal to the one or more processing units;
    the one or more processing units being configured to:
        process the provided information pertaining to the reflected signal to identify one or more faults;
        for each particular fault of the one or more faults, determine the fault type and the distances between the particular fault and two or more inspections modules that have received reflected signals that are potentially from the particular fault,
        for one or more faults having a similar fault type, identify points within the tube system that are at the intersection of a first distance from one inspection module and a second distance from at least one other module to determine potential locations for the one or more faults.

2. The system of claim 1, wherein the similar fault type is a wall loss.

3. The system of claim 1, wherein the signal is an acoustic wave and the inspection module is based on Acoustic Pulse Reflectometry.

4. The system of claim 1, wherein at least one inspection module is coupled to the tube system through a portal in the tube system.

5. The system of claim 1, wherein at least one inspection module is coupled to the tube system by a T-connector placed in-line with one of the tubes of the tube system.

6. The system of claim 1, wherein the plurality of inspection modules are configured such that only one inspection module injects a signal at a time.

7. The system of claim 1, wherein the plurality of inspection modules are configured to inject unique signals such that reflections from one inspection module can be distinguished from reflections and injections of another inspection module.

8. The system of claim 1, wherein each inspection module records the time t1 that a signal is injected and a time t2 at which a reflection is detected.

9. The system of claim 8, wherein each inspection module includes a signal injector interfacing with the one or more processing units; a signal detector interfacing with the processing unit; and an interface tube that is associated with the signal injector and the signal detector and is configured to interface with the tube system, wherein the processing unit being configured to at least partially control the signal injector to cause the injection of a signal into the tube system.

10. The system of claim 1, wherein each inspection module includes sensor configured to detect when the inspection module injects a signal and to detect reflections of the signal.

11. The system of claim 1, wherein the inspection module is directly coupled to the tubing system and the sensor is configured to detect signals in the tubing system and inject signal into the tubing system.

12. A method that identifies the location of a fault in a tube system in which a plurality of inspection modules are coupled to the tube system, the method comprising the actions of:
    a first inspection module transmitting a signal into the tube system at time t1;
    the first inspection module receiving a reflection of the signal from a first fault of a first type at time t2;
    determining the distance L1 from the first inspection module to the first fault;
    identifying a first set of points in the tube system that are at the distance L1 from the first inspection module;
    a second inspection module transmitting a signal into the tube system at time t3;
    the second inspection module receiving a reflection of the signal from a second fault, of the first type, at time t4;
    determining the distance L2 from the second inspection module to the second fault;
    identifying a second set of points in the tube system that are at a distance L2 from the second inspection module; and
    identifying a potential location of a fault of the first type as existing within the intersection of the first set of points and the second set of points.

13. The method of claim 12, wherein the first type of fault is a wall loss.

14. The method of claim 12, wherein the signal is an acoustic wave and the inspection modules are based on Acoustic Pulse Reflectometry.

15. The method of claim 12, wherein the time t1 occurs before the time t3.

16. The method of claim 12, wherein the time t1 and t3 can occur in any order and simultaneously and, the act of the first inspection module transmitting a signal further comprises the act of the first inspection module transmitting a signal that is unique from the signal transmitted by the second inspection module.

17. The method of claim 12, wherein the first injection module and the second injection module transmit signals multiple times over a duration of time and further comprising the actions of detecting changes in the characteristics of the reflected signals.

18. The method of claim 12, further comprising the action of storing information pertaining to the reflected signals for each detected fault.

* * * * *